United States Patent [19]

Ciaglia et al.

[11] Patent Number: 5,653,230
[45] Date of Patent: Aug. 5, 1997

[54] PERCUTANEOUS BALLOON DILATIONAL TRACHEOSTOMY TUBE

[75] Inventors: Pasquale Ciaglia, Utica, N.Y.; Frank J. Fischer, Jr., Bloomington, Ind.

[73] Assignee: Cook Incorporated, Bloomington, Ind.

[21] Appl. No.: 588,986

[22] Filed: Jan. 19, 1996

[51] Int. Cl.⁶ .................................................. A61M 16/00
[52] U.S. Cl. .................. 128/207.15; 128/200.26
[58] Field of Search ...................................... 606/192, 194, 606/198, 191; 128/207.15, 200.26, 207.14, 204.25, 898; 604/118

[56] References Cited

U.S. PATENT DOCUMENTS

| | | |
|---|---|---|
| 3,659,612 | 5/1972 | Shiley et al. . |
| 3,693,624 | 9/1972 | Shiley et al. . |
| 3,734,100 | 5/1973 | Walker et al. . |
| 3,788,326 | 1/1974 | Jacobs . |
| 3,810,474 | 5/1974 | Cross . |
| 3,848,605 | 11/1974 | Harautuneian et al. . |
| 3,862,635 | 1/1975 | Harautuneian . |
| 3,901,246 | 8/1975 | Wallace . |
| 3,971,385 | 7/1976 | Corbett . |
| 3,989,571 | 11/1976 | Harautuneian . |
| 4,018,231 | 4/1977 | Wallace . |
| 4,030,492 | 6/1977 | Simbruner . |
| 4,064,882 | 12/1977 | Johnston et al. . |
| 4,091,816 | 5/1978 | Elam . |
| 4,130,617 | 12/1978 | Wallace . |
| 4,280,492 | 7/1981 | Latham . |
| 4,335,723 | 6/1982 | Patel . |
| 4,361,107 | 11/1982 | Gereg . |
| 4,378,796 | 4/1983 | Milhaud . |
| 4,498,473 | 2/1985 | Gereg . |
| 4,552,558 | 11/1985 | Muto . |
| 4,565,194 | 1/1986 | Weerda et al. . |
| 4,630,606 | 12/1986 | Weerda et al. . |
| 4,632,108 | 12/1986 | Geil . |
| 4,649,914 | 3/1987 | Kowalewski . |
| 4,677,978 | 7/1987 | Melker . |
| 4,722,347 | 2/1988 | Abrams et al. . |
| 4,751,924 | 6/1988 | Hammerschmidt et al. . |
| 4,762,125 | 8/1988 | Leiman et al. . |
| 4,791,920 | 12/1988 | Fauza . |
| 4,791,923 | 12/1988 | Shapiro . |
| 4,796,617 | 1/1989 | Matthews et al. ............. 128/207.15 |

(List continued on next page.)

OTHER PUBLICATIONS

Bradford J. Duft and Eric P. Mirabel, "Principles of Inherency", JTOS, Jul. 1995, pp. 539–570.

Primary Examiner—Michael Buiz
Assistant Examiner—Kevin Truong
Attorney, Agent, or Firm—Richard J. Godlewski

[57] ABSTRACT

A method and device 10 for providing an ostomy 102 through the wall 100 of the trachea are particularly advantageous in allowing the ostomy 102 to be formed atraumatically and to be enlarged without risk of perforating the rear of the trachea. The method employs a balloon catheter 16 including an inflatable balloon 18 and entails: positioning the catheter 16 over a percutaneously inserted wire guide 54; advancing the catheter 16 along the wire guide 54 until the balloon 18 lies across the tracheal wall 100; and inflating the balloon 18 to dilate a portion of the tracheal wall 100 and form an ostomy 102. The method desirably includes the further steps of deflating the balloon 18 and inserting a tracheal tube 20 into the ostomy 102. The method is preferably carried out with a device 10 which includes a dilator tube 12 carrying the catheter 16 and tracheal tube 20 on it. Such a construction allows the dilator tube 12, the balloon catheter 16 and the tracheal tube 20 to be advanced on the wire guide 54 together. The tracheal tube 20 can include an inflatable circumferential cuff 24 for providing a seal between the tracheal tube 20 and the tracheal wall 100. The diameter of the balloon 18 preferably is at least equal to, and more preferably slightly greater than, the maximum diameter of the uninflated cuff 24 to be inserted into the ostomy 102. The present invention is also advantageous in that the close dilation or slight over dilation of the ostomy 102 and the taper of the distal end 14 of the dilator tube 12 protect the cuff 24 from damage during insertion of the tracheal tube 20 through the ostomy 102.

20 Claims, 4 Drawing Sheets

U.S. PATENT DOCUMENTS

| | | |
|---|---|---|
| 4,850,348 | 7/1989 | Pell et al. . |
| 4,856,510 | 8/1989 | Kowalewski . |
| 4,886,059 | 12/1989 | Weber . |
| 4,889,112 | 12/1989 | Schachner et al. . |
| 4,913,139 | 4/1990 | Ballew . |
| 4,913,642 | 4/1990 | Weber . |
| 4,955,375 | 9/1990 | Martinez . |
| 4,976,261 | 12/1990 | Gluck et al. . |
| 5,020,534 | 6/1991 | Pell et al. . |
| 5,054,484 | 10/1991 | Hebeler, Jr. . |
| 5,056,515 | 10/1991 | Abel ................................ 128/207.15 |
| 5,058,580 | 10/1991 | Hazard ............................. 128/207.15 |
| 5,065,755 | 11/1991 | Klafta ............................... 128/207.15 |
| 5,065,757 | 11/1991 | Dragisic et al. . |
| 5,076,268 | 12/1991 | Weber . |
| 5,218,970 | 6/1993 | Turnbull et al. . |
| 5,251,619 | 10/1993 | Lee . |
| 5,265,593 | 11/1993 | Odland . |
| 5,285,777 | 2/1994 | Beckwith . |
| 5,287,848 | 2/1994 | Cubb et al. . |
| 5,311,864 | 5/1994 | Huerta . |
| 5,315,992 | 5/1994 | Dalton . |
| 5,360,003 | 11/1994 | Capistrano . |
| 5,379,765 | 1/1995 | Kajiwara et al. . |
| 5,392,774 | 2/1995 | Sato . |

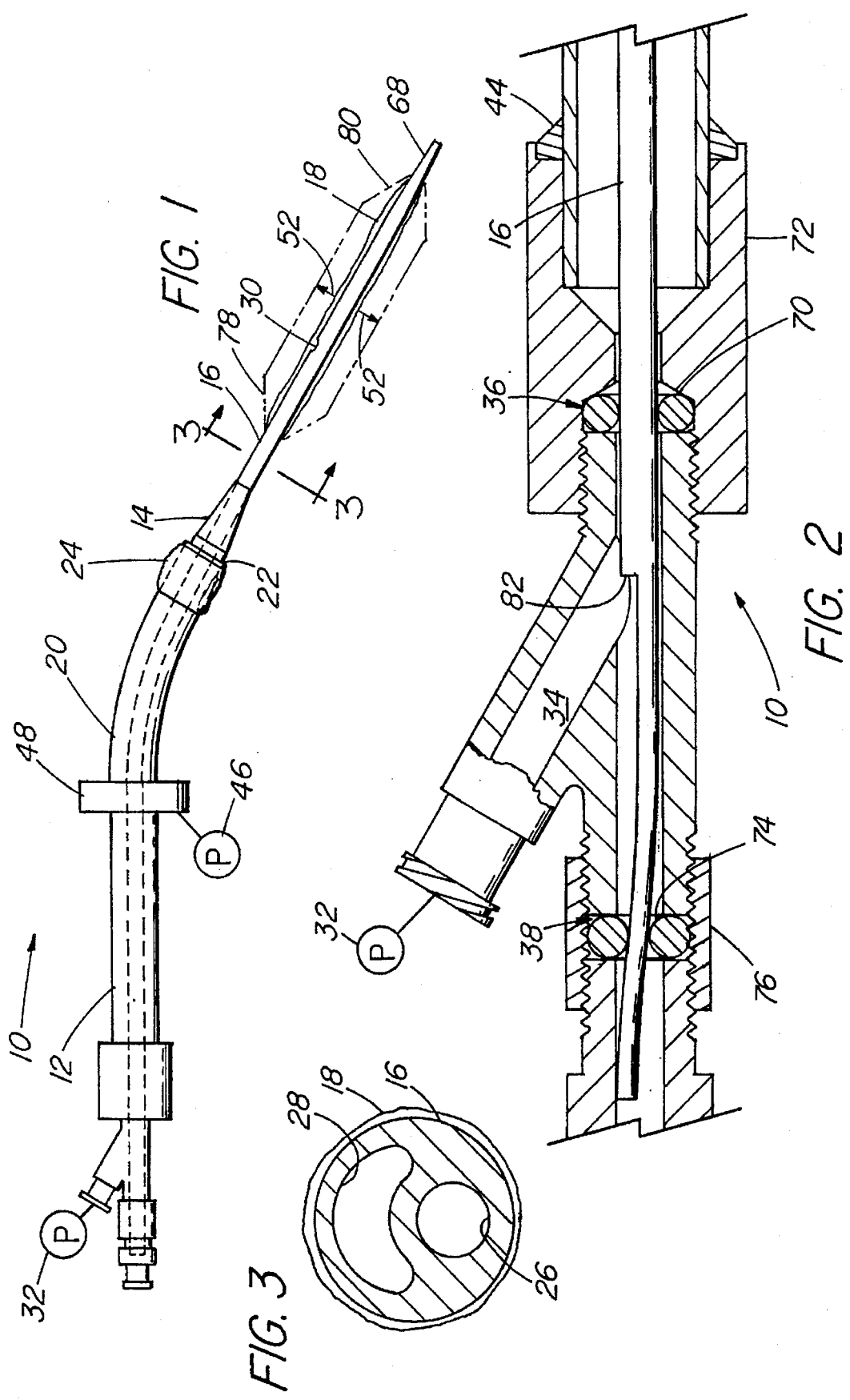

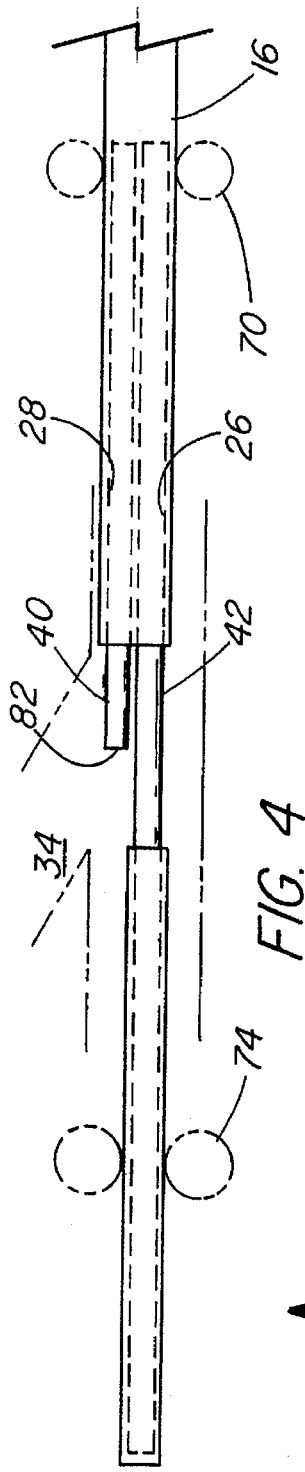
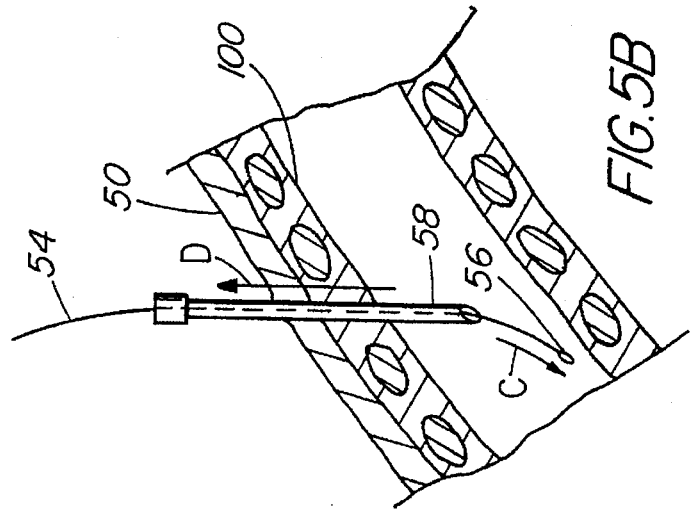
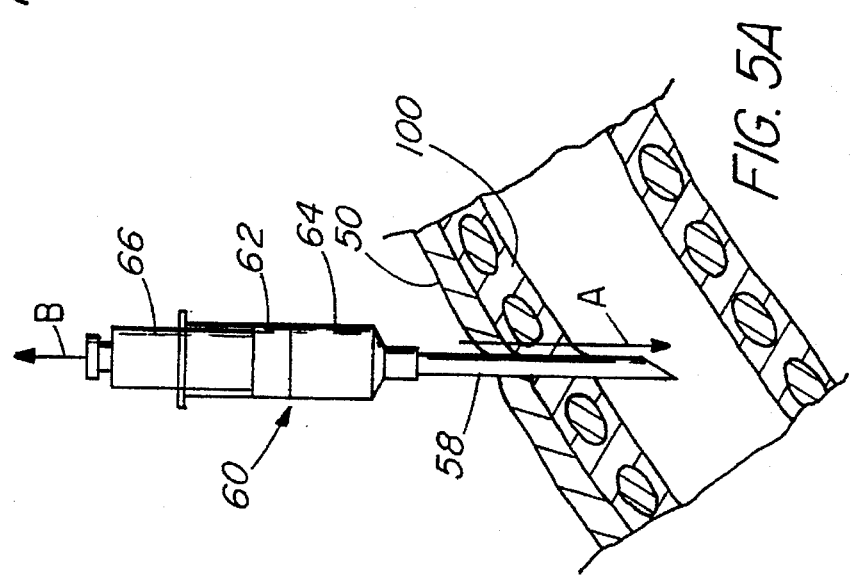

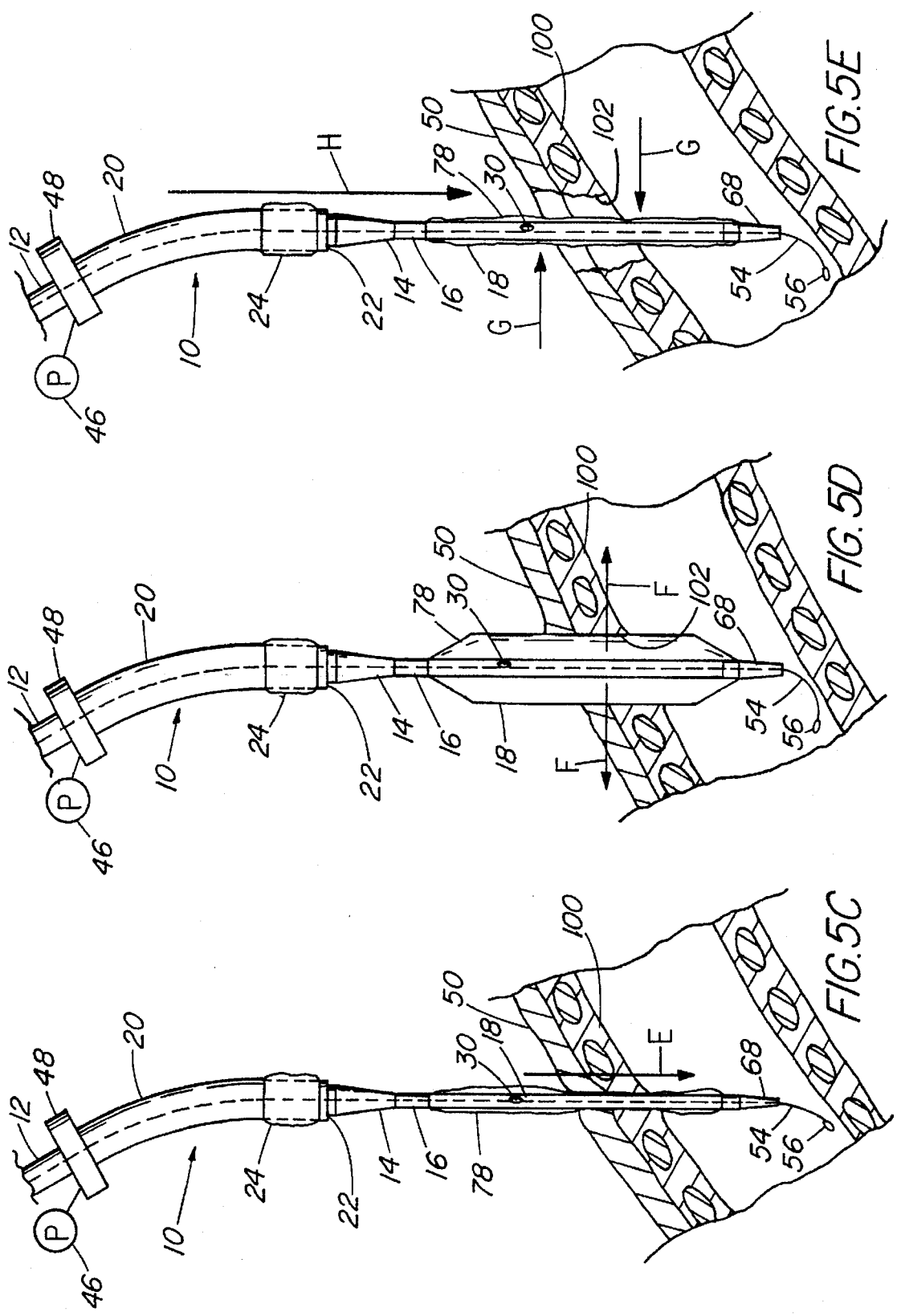

5,653,230

PERCUTANEOUS BALLOON DILATIONAL TRACHEOSTOMY TUBE

TECHNICAL FIELD

This invention relates generally to medical devices percutaneously accessing a patient's air passageway and atraumatically dilating an opening thereto, and in particular, to a dilator for forming an ostomy in a tracheal wall.

BACKGROUND OF THE INVENTION

The establishment of an adequate air passageway is the first critical step in maintaining the ability of a seriously ill or injured patient to breathe, or in performing resuscitation on a patient unable to breathe. Endotracheal intubation (the placement of a tube through the nostrils or mouth and into the trachea itself) is the preferred method for establishing an air passageway when the trachea, nostrils and/or mouth are free of obstruction. When any such obstruction is present, however, endotracheal intubation is not possible, so that some other passageway for airflow must be established.

The most direct way to provide an air passageway under these circumstances is to form an ostomy or opening in the tracheal wall, and once formed, to keep the ostomy open by inserting a tracheal tube into it. Conventional tracheal tubes often include an open distal aperture and a circumferential inflatable cuff. The cuff provides a seal between the tracheal wall and the tracheal tube at a location cranial to the distal aperture. The seal so provided has several advantages, most importantly, that the seal prevents the intrusion blood, tissue or foreign matter into the lower trachea, bronchi and lungs, while permitting complete control and monitoring of the airflow established through the tracheal tube, including the provision of positive pressure ventilation. While the cuff is thin and flexible enough to provide a good seal, its thinness and flexibility make it easily subject to damage or puncture during introduction of the tracheal tube into the ostomy.

Several methods and devices are known for forming or enlarging an ostomy in a tracheal wall, and each are subject to their own advantages and drawbacks. For example, tracheostomy and cricothyrotomy procedures have been performed by using a scalpel to make an incision in the neck. Such procedures often entail a high degree of surgical skill to perform successfully, particularly since it is vital to locate and avoid unintentional severing of the blood vessels in'the area. These procedures can even require the surgeon to cut through several blood vessels and ligate (tie) them to the trachea, in order to achieve an adequately large ostomy. The length of time needed to perform these procedures (often, on the order of half an hour) is poorly suited to emergency treatment, when prompt restoration of the air passageway is critical. Moreover, the use of a scalpel to fully form an ostomy potentially causes undue trauma to the tissues surrounding the ostomy site, and can result in the formation of an unduly large or oversized opening in the soft tissue of the neck.

To minimize such trauma, it has been found desirable to initially incise only a small opening, and thereafter enlarge the opening with further dilation. For example, one prior technique for dilating an ostomy includes the use of a wire guide to facilitate the introduction of a dilator into the trachea. As disclosed in U.S. Pat. No. 4,677,978 (Melker, Jul. 7, 1987), such a technique involves the insertion of a needle and an over-the-needle catheter into the trachea. The needle is removed and the catheter replaced with a wire guide. A tapered, elongated, tubular dilator is positioned over the wire guide and introduced into the trachea. A drawback of this technique is that it requires the preliminary use of a scalpel to make an incision through the skin and cricothyroid membrane so that the needle can be inserted into the trachea. Even though intended to be performed in an emergency situation, the technique entails the sequential manipulation of several devices by the physician, which is time consuming and complicates the procedure.

The procedure disclosed in U.S. Pat. No. 4,889,112 (Schachner et al., Dec. 26, 1989) eliminates the use of the catheter and involves placing a wire guide through the needle itself. The ostomy formed by the needle is then dilated by the use of a device having a handle and a nose, the nose extending laterally from the axis of the handle. The nose has two jaws that spread apart for separating the tissue surrounding the ostomy, and the device is introduced into the trachea by positioning the elongated, tapered nose over the wire guide. While this type of device offers more powerful dilation than is possible with elongated tubular dilators, a problem with this device is that the unguarded nose must be inserted into the trachea with precision, and must be manipulated at an angle, in order to avoid perforating the posterior tracheal wall.

Another prior art technique for dilating an ostomy is the use of a tapered, elongated, tubular dilator or a series of telescopically positionable, tapered dilators with increasingly larger diameters. A problem with these dilators is that each dilator presents a pointed distal end to the posterior tracheal wall when introduced into the trachea. The risk of injury to the trachea is compounded by the toughness of the tracheal membrane, which resists the introduction of medical devices. Introducing these elongated dilators requires the application of considerable force. A physician must push the dilator into the trachea yet avoid puncturing the posterior tracheal wall.

The tracheal ostomy speculum of one of the inventors herein, disclosed in U.S. Pat. No. 5,217,007 (Ciaglia, Jun. 8, 1993), fully meets the problem of perforation of the posterior tracheal wall. The particularly disclosed speculum is not used with a wire guide, but instead includes a flexible and curved distal end on one of the members, and a cannula sized for extension through that end. The tip of the cannula is exposed and the cannula straightens the curved distal end during penetration of the tracheal wall. The cannula is retracted as penetration advances, however, so that only the flexible and curved distal end meets the posterior tracheal wall when the speculum is used to dilate the ostomy. Trauma to the posterior wall is thus avoided. While this speculum is admirably useful for its intended purpose, its use does require some degree of grip strength from the physician. Of course, the speculum provides no protection for the cuff on the tracheal tube to be inserted into the ostomy formed by the speculum. Moreover, it would be advantageous to reduce the cost or complexity of this or any other device for forming or dilating a tracheal ostomy.

It should therefore be clear that it would be highly desirable to find methods and devices for forming and dilating an ostomy in a tracheal wall which are atraumatic, that is, which avoid or substantially avoid the trauma and damage to the tracheal wall encountered in many prior methods and devices. It would also be highly desirable to find methods and devices which permit the enlargement of a formed ostomy without risk of perforating the rear of the trachea. It would further be desirable to find methods and devices which protect the cuff of a tracheal tube from damage during the insertion of the tracheal tube through the ostomy.

SUMMARY OF THE INVENTION

The foregoing problems are solved and a technical advance is achieved in an illustrative method and device for providing an ostomy through the wall of a trachea. The method employs a balloon catheter including an inflatable balloon, and comprises the steps of percutaneously inserting the tip of a wire guide through the tracheal wall so that the wire guide lies across the tracheal wall; positioning the catheter over the wire guide; advancing the catheter along the wire guide until the balloon lies across the tracheal wall; and inflating the balloon to atraumatically dilate a portion of the tracheal wall, thereby forming the desired dilated ostomy. Preferably, a hollow needle is first inserted through the tracheal wall, the tip of the wire guide passed through the needle, and the needle removed while the wire guide is allowed to remain in place across the tracheal wall. Also preferably, the method includes the further steps of deflating the balloon and inserting a tracheal tube into the ostomy.

The tracheal tube can be of any conventional construction and can include an inflatable circumferential cuff on it, providing a seal between the tracheal tube and the tracheal wall. The tracheal tube can be a separate element positioned in the open ostomy after the balloon is removed from the dilated ostomy. However, the method of the present invention is most preferably carried out employing a device particularly adapted to carry and protect the tracheal tube and its cuff during insertion of the tracheal tube into the ostomy. The device is a percutaneous balloon dilational tracheostomy tube which comprises a dilator tube carrying the catheter and tracheal tube on it. Such a construction allows the dilator tube, the balloon catheter and the tracheal tube to be advanced on the wire guide together, without longitudinal movement of the dilator tube, the balloon catheter and the tracheal tube relative to one another. Advancement of the device along the wire guide thus introduces the tracheal tube into the ostomy.

The diameter of the balloon preferably is at least equal to, and more preferably is slightly greater than, the maximum diameter of any portion of the tracheal tube (such as the uninflated cuff) to be inserted into the ostomy. Damage to the cuff during insertion is thus avoided.

In a first aspect, then, the present invention is directed to a device for forming an ostomy in a tracheal wall, useful in conjunction with a wire guide percutaneously positionable across the tracheal wall, the device comprising:

a dilator tube having a distal end; and a balloon catheter carried by the dilator tube, the balloon catheter including an inflatable balloon extending from the distal end of the dilator tube; wherein the dilator tube and the balloon catheter are advanceable along the wire guide, and wherein the balloon is inflatable so as to atraumatically dilate a portion of the tracheal wall and thereby form an ostomy in the tracheal wall. Additional features of this first aspect of the invention are disclosed in more detail below.

In a second aspect, the present invention is directed to a device for forming an ostomy in a tracheal wall, useful in conjunction with a wire guide percutaneously positionable across the tracheal wall, the wire guide including an atraumatic tip, and the device comprising: a dilator tube having a tapered distal end; a balloon catheter carried by the dilator tube, the balloon catheter including an inflatable balloon extending from the distal end of the dilator tube, a longitudinally extending bore for supplying a fluid under pressure to the balloon, and a longitudinal throughbore dimensioned to receive the wire guide therein; a tracheal tube carried by the dilator tube adjacent to the distal end of the dilator tube, the tracheal tube comprising a distal aperture and an inflatable circumferential cuff adjacent to the distal aperture; and a hollow needle for positioning the wire guide across the tracheal wall; wherein the balloon, when inflated, has a diameter equal to or greater than the diameter of the circumferential cuff of the tracheal tube when the circumferential cuff is uninflated; wherein the dilator tube, the balloon catheter and the tracheal tube are coaxially disposed and are adapted for advancement along the wire guide together, without any longitudinal movement of the dilator tube, the balloon catheter and the tracheal tube relative to one another during advancement; and wherein the balloon is inflatable so as to atraumatically dilate a portion of the tracheal wall and thereby form an ostomy in the tracheal wall.

In a final aspect, the present invention is directed to a percutaneous method of forming an ostomy in a tracheal wall, employing a balloon catheter including an inflatable balloon, comprising the steps of: percutaneously inserting the tip of a wire guide through the tracheal wall so that the wire guide lies across the tracheal wall; positioning the balloon catheter over the wire guide; advancing the balloon catheter along the wire guide until the balloon lies across the tracheal wall; and inflating the balloon to atraumatically dilate a portion of the tracheal wall and thereby form an ostomy in the tracheal wall. Additional features of this aspect of the present invention are also disclosed in more detail below.

The method and device of the present invention possess several advantages over the prior methods and devices for forming or dilating ostomies. The present invention allows the ostomy to be formed atraumatically, and dilated without risk of perforating the posterior wall of the trachea. Moreover, the close dilation or slight overdilation of the ostomy provided by the specified diameter of the balloon used for dilation, and the taper on the distal end of the dilator tube, facilitate insertion of the tracheal tube into the ostomy and protect the cuff of the tracheal tube from damage during insertion. The present invention is also relatively less expensive, and simpler in construction and use, than many prior ostomy dilators.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a side view of the preferred embodiment of the present invention;

FIG. 2 is a cross-sectional view of a portion of the preferred embodiment of the present invention;

FIG. 3 is a cross-sectional view taken along line 3—3 of FIG. 1;

FIG. 4 is a partial view of a portion of the preferred embodiment of the present invention; and FIGS. 5A through 5G are partial views of a surgical procedure performed with the preferred embodiment of the present invention.

DETAILED DESCRIPTION

Figure 5G:
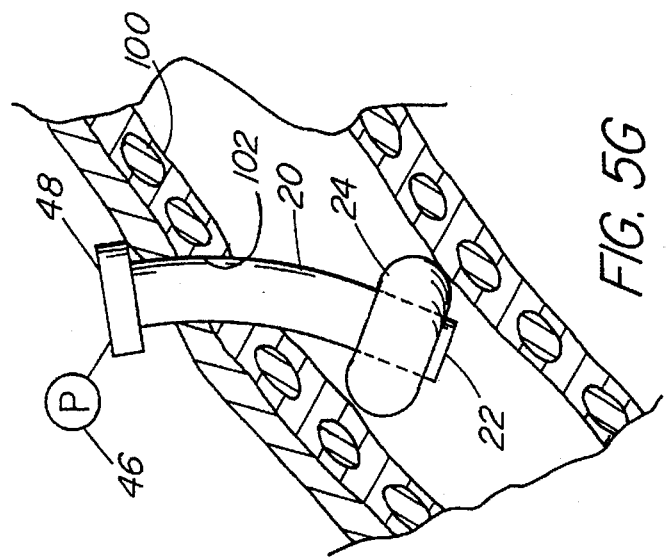

With reference first to FIG. 1, the preferred embodiment of the present invention for forming an ostomy in a tracheal wall is shown as percutaneous balloon dilational tracheostomy tube or device 10, useful in conjunction with a percutaneous wire guide (not shown in FIG. 1 but described in more detail below). The device 10 first comprises a hollow dilator tube 12 having a tapered distal end 14. The device 10 also comprises a balloon catheter 16 coaxially carried by and disposed in the dilator tube 12. The catheter 16 includes an inflatable balloon 18 extending from the distal end 14 of the dilator tube 12. The catheter 16 has a perforate atraumatic tip 68 distal to the balloon 18, opposite the distal end 14 of the dilator tube 12. The dilator tube 12 and catheter 16 are composed of medical grade, synthetic materials. Except for the balloon 18, the balance of the catheter 16 is preferably composed of a relatively flexible and slightly elastic material, while the dilator tube is preferably composed of a somewhat rigid but somewhat resilient material.

The balloon 18 of the catheter 16 is desirably composed of PET or another flexible but inelastic material. The balloon 18 can conveniently have an average burst pressure of about seventeen bars. Preferably, as shown in phantom, the balloon 18 is generally cylindrical in shape when inflated, and has a pair of proximal and distal ends 78 and 80, respectively, tapered at an angle of about 20 degrees with respect to the longitudinal axis of the catheter 16. The inflated diameter of the balloon 18 (indicated by the arrows 52) is selected in view of the size of ostomy to be formed. The balloon 18 is about 60 mm long between the ends 78 and 80.

The dilator tube 12 and the balloon catheter 16 are adapted for advancement along a wire guide as mentioned above. As more clearly shown in FIGS. 3 and 4, the catheter 16 includes a longitudinal throughbore 26 dimensioned to receive the wire guide therein, the tip 68 of the catheter 16 allowing entry of the wire guide into the throughbore 26. The catheter 16 also includes a longitudinally extending bore 28 for supplying a fluid under pressure for inflating the balloon 18. The bore 28 is open to a chamber 34 which fluidly connects the bore 28 to a supply of pressurized fluid 32, the fluid supply 32 being indicated in only a general manner. A port 30 in the bore 28, beneath and open to the balloon 18, completes the fluid communication of the balloon 18 with the fluid supply 32. Preferably, the fluid provided by the fluid supply 32 is saline solution at about three bars pressure, which is adequate to atraumatically dilate a portion of a tracheal wall and thereby form an ostomy in the tracheal wall.

With reference now to FIGS. 2 and 4, the chamber 34 is defined by and sealed by a distal seal 36 and a proximal seal 38. The seals 36 and 38 comprise a pair of threaded compression fittings 72 and 76 which trap and compress a pair of 0-rings 70 and 74, respectively, against the catheter 16. The distal one of the compression fittings, for example, the fitting 72, is connected to the dilator tube 12 in any convenient manner, for example, by a bead of adhesive 44.

A first supportive metal tube 40 extends into the chamber 34 from, and is contained partly in, the bore 28. A second supportive metal tube 42 continues the throughbore 26 in the chamber 34. The supportive metal tubes 40 and 42 prevent the 0-rings 70 and 74 from collapsing the throughbore 26 and bore 28 when the compression fittings 72 and 76 are tightened. The first metal tube 40 includes a proximal end 82 open to and contained in the chamber 34.

It is preferred that the degree of compression provided by the seals 36 and 38 be fixed prior to use of the device 10, and in particular, fixed during manufacture of the device 10. Such fixing can be performed by applying an adhesive to the compression fittings 72 and 76. However, the use of the compression fittings 72 and 76 can alternatively allow some slight selective longitudinal movement of the catheter 16 with respect to the dilator tube 12. The length of movement is subject to the need to keep the proximal end 82 of the first metal tube 40 within the chamber 34. Such movement can be achieved merely by loosening both of the compression fittings 72 and 76, manually sliding the catheter 16 with respect to the dilator tube 12, and tightening both of the compression fittings 72 and 76. For the device 10 sized to an adult patient, the amount of movement is such as to allow the proximal end 78 of the balloon 18 to lie between about 2 mm and about 12 mm from the distal end 14 of the dilator tube 12. The balloon catheter 16 is thus telescopically received in the dilator tube 12. The usefulness of such selective movement is described in more detail below, in connection with the method of the present invention.

As indicated above, the purpose of forming an ostomy in the tracheal wall is to allow the insertion of a tracheal tube 20 through the tracheal wall, so as to establish an air passageway for the patient. The device 10 as described so far can be used quite well for establishing an ostomy for the insertion of a separate tracheal tube 20 standing alone. However, it is particularly preferred that the device 10 comprise the tracheal tube 20 as well, coaxially carried on the dilator tube 12 adjacent to its distal end 14.

The tracheal tube 20 is composed of a medical grade, substantially rigid synthetic material, for example, radiopaque polyvinyl chloride. The tracheal tube 20 possesses a permanent curve which facilitates its introduction into an ostomy in the tracheal wall. The tracheal tube 20 comprises a distal aperture 22 open to the trachea and lungs of the patient, as well as an inflatable circumferential cuff 24 positioned adjacent to the distal aperture 22 of the tracheal tube 20. As is conventional, the cuff 24 is desirably a thin wall, high volume, low pressure cuff, composed of a flexible and somewhat elastic material; this permits the cuff 24 to establish a good seal between the tracheal tube 20 and the trachea of the patient, cranial to the distal aperture 22 of the tracheal tube 20.

The tracheal tube 20 can further comprise a flange 48 for abutment against the skin of the patient when the tracheal tube 20 is inserted in the ostomy. The flange 48 is represented diagrammatically in the Figures as a flat disk, but can of course be a conventional swivel neck plate, pivoted with respect to the body of the tracheal tube 20. A supply 46 of low-pressure fluid (such as air) for inflating and deflating the cuff 24 is also represented diagrammatically in the Figures, and includes not only a fluid source or reservoir (not shown) but also any conventional tubes, bores or conduits employed to fluidly connect the cuff 24 to the fluid supply 46. The nature of such elements is well known and is believed not to be critical to the present invention, and therefore are not further described here.

The tracheal tube 20 possesses conventional dimensions suited to the patient into whom it will be introduced. For example, for adult patients, the tracheal tube 20 can typically have an outside diameter of about 8.5 to about 13.0 mm, and an inside diameter of about 5.0 to 9.0 mm. A tracheal tube 20 with an outside diameter of about 12.0 mm and an inside diameter of about 8.5 mm will be used as an example herein, merely by way of explanation, and not as a limitation of the invention.

The diameter of the dilator tube 12 and the diameter of the balloon 18 when inflated are selected to match the size of the tracheal tube 20 being inserted. For example, it is preferable but not essential that the diameter of the dilator tube 12 be very close to the inside diameter of the tracheal tube 20. Indeed, these two diameters can possess the same nominal value, that is, the dilator tube 12 can have the same nominal 8.5 mm diameter as the nominal 8.5 mm inside diameter of the tracheal tube 20. The slight resiliency of the dilator tube 12 permits this close tolerance; however, it may be advantageous to apply a water-soluble jelly or other lubricant over the dilator tube 12 to ensure that the tracheal tube 20 does not become stuck on the dilator tube 12.

It is also preferable that the balloon 18, when inflated, have a diameter equal to or slightly greater than the outside diameter of the tracheal tube 20 and uninflated cuff 24. For use with the tracheal tube 20 having an outside diameter of 12.0 mm, the balloon 18 should have a diameter when inflated of 12.0 mm, or slightly more, perhaps 0.5 to 1.0 mm more. This close sizing or slight oversizing of the balloon diameter as compared to the tracheal tube diameter ensures that the ostomy formed by the balloon 18 will be large enough to prevent damage to the cuff 24 during insertion of the tracheal tube 20 into the ostomy.

It should be noted that any separate tracheal tube 20 not carried by the dilator tube 12 can have the same features and construction as disclosed above. In such a case, the diameter of the balloon 18 when inflated should be only equal to, and not greater than, the outside diameter of the tracheal tube 20.

It is particularly advantageous that the tracheal tube 20 be coaxially carried by the dilator tube 12. In such a case, the dilator tube 12, the balloon catheter 16 and the tracheal tube 20 are adapted for advancement along a wire guide together, without any longitudinal movement of any of them relative to one another during such advancement. Such movement as a single unit reduces the number of manipulative steps necessary to introduce the tracheal tube 20 into the ostomy, and thereby making the introduction faster and easier to perform.

Performance of the percutaneous method of the present invention for forming an ostomy 102 in a tracheal wall 100 can now be readily understood. The cricothyroid membrane of the tracheal wall 100 between the thyroid and cricoid cartilages is first palpated, and a slight incision is made with a scalpel through the skin 50 and the membrane. As shown in FIG. 5A, a hollow needle 58 carried by a syringe 60 is inserted in the direction of arrow A through the tracheal wall 100 at the incision, while gentle back pressure is applied to the plunger 66 of the syringe 60 by drawing the plunger 66 in the direction of arrow B. A fluid 64 is contained in the barrel 62 of the syringe 60, and this back pressure causes bubbles to appear in the fluid 64 as a positive visual indication when the needle 58 has fully penetrated the tracheal wall 100.

Once the needle 58 has penetrated the tracheal wall 100, the syringe 60 is detached from the needle 58, leaving the needle 58 in position across the tracheal wall 100. As shown in FIG. 5B, the atraumatic tip 56 of a wire guide 54 is then percutaneously inserted through the tracheal wall 100 by passing the atraumatic tip 56 through the interior of the hollow needle 58, in the direction of arrow C. The hollow needle 58 is then removed from the tracheal wall 100 by withdrawing it in the direction of arrow D, while allowing the wire guide 54 to remain in place across the tracheal wall 100.

With reference now to FIG. 5C, the next step in the method of the present invention is to position a balloon catheter 16, preferably the one incorporated into the device 10 disclosed above, over the wire guide 54. Such positioning is carried out by placing the atraumatic tip 68 of the catheter 16 over the wire guide 54 so that the wire guide 54 is received in the longitudinal throughbore 26 in the catheter 16. If desired (for example, for improved visibility of the site of the ostomy 102), the catheter 16 may be manually extended slightly from the distal end 14 of the dilator tube 12 by loosening the compression fittings 72 and 76 about the catheter 16, slightly sliding the catheter 16 longitudinally with respect to the dilator tube 12, and tightening the compression fittings 72 and 76 sufficiently to prevent leakage of pressurized fluid around the O-rings 70 and 74. The balloon catheter 16, carried by the device 10, is then advanced along the wire guide 54 in the direction of arrow E until the inflatable balloon 18 of the catheter 16 lies fully across the tracheal wall 100.

The fluid supply 32 is then activated to provide pressurized fluid to the chamber 34, the longitudinally extending bore 28 and the port 30, inflating the balloon 18 in the direction of arrows F of FIG. 5D to atraumatically dilate a portion of the tracheal wall 100, and thereby form an ostomy 102 in the tracheal wall 100. Conveniently, the fluid from the fluid supply 32 is saline solution at about three bars pressure. Once the ostomy 102 is formed, the balloon 18 is deflated in the direction of arrows G of FIG. 5E, by withdrawing fluid from the chamber 34, the bore 28 and the port 30.

The ostomy 102 is thus ready for insertion of the tracheal tube 20 into it. Such insertion can be carried out in several ways. If the tracheal tube 20 is a separate tube not carried by the dilator tube 12, the balloon catheter 16 and the wire guide 54 can be completely withdrawn from the ostomy 102 and the tracheal tube 20 manually inserted into the ostomy 102. If the tracheal tube 20 is carried by the dilator tube 12, it is possible to hold the device 10 in the position shown in FIG. 5E, and manually advance and insert only the tracheal tube 20 into the ostomy 102. The balloon catheter 16 and the wire guide 54 would then be withdrawn through the ostomy together.

Most preferably, however, the tracheal tube 20 is inserted into the ostomy 102 by advancing the dilator tube 12, the balloon catheter 16 and the tracheal tube 20 together along the wire guide 54 in the direction of arrow H of FIG. 5E, until the flange 48 on the tracheal tube 20 abuts the skin 50 over the tracheal wall 100. Such advancement is carried out without any longitudinal movement of the dilator tube 12, the balloon catheter 16 and the tracheal tube 20 relative to one another. Movement of these elements together is advantageous because the dilator tube 12 provides a smooth transitional taper for insertion of the tracheal tube 20, while the catheter 16 acts as an insertion guide for the tracheal tube 20; each of these serves to protect the cuff 24 from damage during insertion of the tracheal tube 20 into the ostomy 102. It may be desirable, prior to such movement, to retract the deflated balloon 18 towards the distal end 14 of the dilator tube 12, if the catheter 16 was previously extended from the distal end 14 of the dilator tube 12. Such retraction would be performed by loosening the compression fittings 72 and 76, manually moving the catheter 16 slightly back into the distal end 14 of the dilator tube 12, and tightening the fittings 72 and 76. When the tracheal tube 20 has been inserted into the ostomy 102 in the tracheal wall 100, the dilator tube 12, the balloon catheter 16 and the wire guide 54 are withdrawn in the direction of arrow I of FIG. 5F.

Figure 5F:
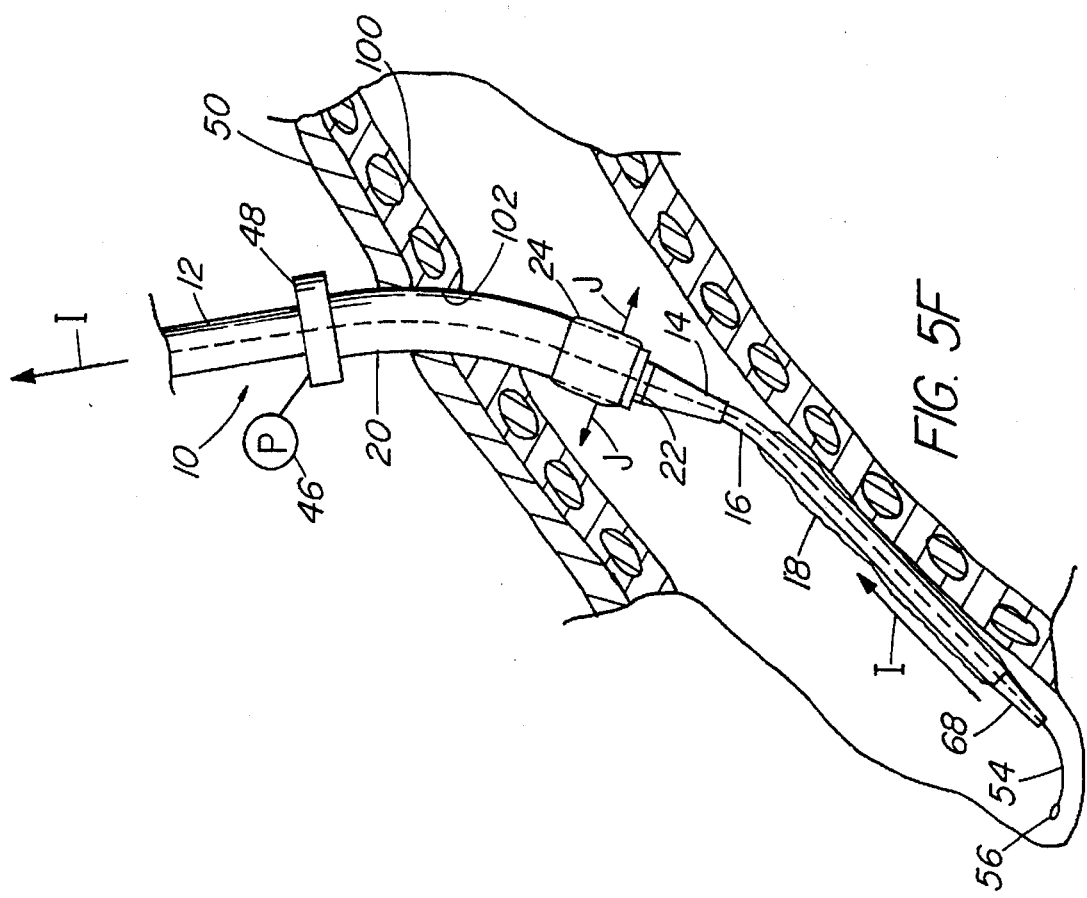

Without regard to which of these methods are employed for positioning the tracheal tube in the ostomy 102, after such positioning the circumferential cuff 24 of the tracheal tube 20 is inflated by supplying pressurized air or other fluid from the fluid supply 46 to provide a seal between the tracheal wall 100 and the tracheal tube 20. This seal is cranial to the distal aperture 22 of the tracheal tube 20, preventing the intrusion of foreign matter into the trachea and lungs, and permitting the control of respiration through the tracheal tube 20. The resulting arrangement of the tracheal tube 20 in the ostomy 102 is shown in FIG. 5G.

Desirably, a conventional disposable intubation inner sleeve and connector (not shown) can then be inserted into the tracheal tube 20 for the usual and well-known purposes.

It is highly desirable that the fit of the tracheal tube 20 in the ostomy 102 be relatively tight. It is also highly desirable, however, that the circumferential cuff 24 of the tracheal tube 20 not be damaged during its passage through the ostomy 102. Accordingly, the method is preferably carried out with a balloon 18 whose diameter, when inflated, is equal to or slightly greater than the diameter of the tracheal tube 20 and the diameter of the cuff 24 when the cuff 24 is uninflated. The insertion of the tracheal tube 20 can be aided by evacuation of the cuff 24 during insertion, minimizing its diameter, as well as by the application of an appropriate water-soluble jelly or other lubricant to the outside of the tracheal tube 20 and to the cuff 24 before insertion. It may also be helpful to apply the water-soluble jelly or other lubricant to the outside of the dilator tube 12, that is, between the dilator tube 12 and the tracheal tube 20, making it easier to withdraw the dilator tube 12 from the inserted tracheal tube 20. The inserted tracheal tube 20 can be taped or strapped to the neck of the patient in the conventional manner.

It should be evident from the above discussion that the device 10 of the present invention can comprise not only the combination of the dilator tube 12 and the balloon catheter 16, and optionally the tracheal tube 20, but can also comprise either or both of the wire guide 54 and the hollow needle 58 employed to position the catheter balloon 18 across the tracheal wall 100.

The method and device of the present invention possess several advantages over the prior methods and devices for forming or dilating ostomies. The present invention allows the ostomy 102 to be formed and dilated atraumatically without risk of perforating the posterior wall of the trachea. Moreover, the close dilation or slight overdilation of the ostomy 102 provided by the balloon 18 protects the cuff 24 from damage during insertion of the tracheal tube 20 into the ostomy 102. Telescoping movement of the balloon catheter 16 within the dilator tube 12, although perhaps not preferred, does allow the health practitioner to obtain an improved initial view of the ostomy site without sacrificing protection of the cuff 24 later in the procedure. The present invention is also relatively less expensive, and simpler in construction and use, than many prior ostomy dilators.

Any undisclosed details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

INDUSTRIAL APPLICABILITY

The present invention is useful in the performance of surgical procedures, and therefore finds applicability in human and veterinary medicine.

It is to be understood, however, that the abovedescribed device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts and steps.

What is claimed is:

1. A device (10) for forming an ostomy (102) in a tracheal wall (100), useful in conjunction with a wire guide (54) percutaneously positionable across the tracheal wall (100), and the device (10) comprising:
    a dilator tube (12) having a distal end (14); and
    a balloon catheter (16) carried by the dilator tube (12), the balloon catheter (16) including an inflatable balloon (18) extending from the distal end (14) of the dilator tube (12);
    wherein the dilator tube (12) and the balloon catheter (16) are advanceable along the wire guide (54), and wherein the balloon (18) is adapted to atraumatically dilate a portion of the tracheal wall (100) and form an ostomy (102) in the tracheal wall (100) upon inflation Of the balloon (18).

2. The device (10) according to claim 1, further comprising a tracheal tube (20) carried by the dilator tube (12) adjacent to the distal end (14) of the dilator tube (12).

3. The device (10) according to claim 2, wherein the tracheal tube (20) comprises a distal aperture (22) and an inflatable circumferential cuff (24) adjacent to the distal aperture (22).

4. The device (10) according to claim 3, wherein the balloon (18), when inflated, has a diameter equal to or greater than the diameter of the circumferential cuff (24) of the tracheal tube (20) when the circumferential cuff (24) is uninflated.

5. The device (10) according to claim 3, wherein the dilator tube (12), the balloon catheter (16) and the tracheal tube (20) are adapted for advancement along the wire guide (54) together, without any longitudinal movement of the dilator tube (12), the balloon catheter (16) and the tracheal tube (20) relative to one another during advancement.

6. The device (10) according to claim 1, further comprising an atraumatic tip (56) on the wire guide (54).

7. The device (10) according to claim 1, further comprising a hollow needle (58) for positioning the wire guide (54) across the tracheal wall (100).

8. The device (10) according to claim 1, wherein the dilator tube (12) and the balloon catheter (16) are coaxially disposed.

9. The device (10) according to claim 1, wherein the balloon catheter (16) includes a longitudinal throughbore (26) dimensioned to receive the wire guide (54) therein.

10. The device (10) according to claim 1, wherein the balloon catheter (16) is telescopically received and selectively moveable in the dilator tube (12).

11. The device (10) according to claim 1, wherein the distal end (14) of the dilator tube (12) is tapered.

12. The device (10) according to claim 1, wherein the balloon catheter (16) includes a longitudinally extending bore (28) for supplying a fluid under pressure to the balloon (18).

13. A device (10) for forming an ostomy (102) in a tracheal wall (100), useful in conjunction with a wire guide (54) percutaneously positionable across the tracheal wall (100), the wire guide (54) including an atraumatic tip (56), and the device (10) comprising:
    a dilator tube (12) having a tapered distal end (14);
    a balloon catheter (16) carried by the dilator tube (12), the balloon catheter (16) including an inflatable balloon (18) extending from the distal end (14) of the dilator tube (12), a longitudinally extending bore (28) for supplying a fluid under pressure to the balloon (18), and a longitudinal throughbore (26) dimensioned to receive the wire guide (54) therein;

a tracheal tube (20) carried by the dilator tube (12) adjacent to the distal end (14) of the dilator tube (12), the tracheal tube (20) comprising a distal aperture (22) and an inflatable circumferential cuff (24) adjacent to the distal aperture (22); and a hollow needle (58) for positioning the wire guide (54) across the tracheal wall (100);

wherein the balloon (18), when inflated, has a diameter equal to or greater than the diameter of the circumferential cuff (24) of the tracheal tube (20) when the circumferential cuff (24) is uninflated;

wherein the dilator tube (12), the balloon catheter (16) and the tracheal tube (20) are coaxially disposed and are adapted for advancement along the wire guide (54) together, without any longitudinal movement of the dilator tube (12), the balloon catheter (16) and the tracheal tube (20) relative to one another during advancement; and wherein the balloon (18) is adapted to atraumatically dilate a portion of the tracheal wall (100) and form an ostomy (102) in the tracheal wall (100) upon inflation of the balloon (18).

14. A percutaneous method of forming an ostomy (102) in a tracheal wall (100), employing a balloon catheter (16) including an inflatable balloon (18) adapted to atraumatically dilate a portion of the tracheal wall (100) upon inflation of the balloon (18), comprising the steps of:

percutaneously inserting the tip (56) of a wire guide (54) through the tracheal wall (100) so that the wire guide (54) lies across the tracheal wall (100);

positioning the balloon catheter (16) over the wire guide (54);

advancing the balloon catheter (16) along the wire guide (54) until the balloon (18) lies across the tracheal wall (100); and inflating the balloon (18) while it lies across the tracheal wall (100) to atraumatically dilate a portion of the tracheal wall (100) and form an ostomy (102) in the tracheal wall (100).

15. The method according to claim 14, wherein the percutaneous inserting step comprises the steps of:

inserting a hollow needle (58) through the tracheal wall (100);

passing the tip (56) of the wire guide (54) through the hollow needle (58); and removing the hollow needle (58) from the tracheal wall (100) while allowing the wire guide (54) to remain in place across the tracheal wall (100).

16. The method according to claim 14, comprising the further steps of:

deflating the balloon (18); and inserting a tracheal tube (20) into the ostomy (102) formed by inflation of the balloon (18).

17. The method according to claim 16, wherein the inflating step is carried out with a balloon (18) whose diameter, when inflated, is equal to or greater than the maximum diameter of any portion of the tracheal tube (20) inserted into the ostomy (102).

18. The method according to claim 16, wherein the inserting step is carried out with a tracheal tube (20) comprising a distal aperture (22), and an inflatable circumferential cuff (24) adapted to provide a seal between the tracheal wall (100) and the tracheal tube (20) at a location cranial to the distal aperture (22).

19. The method according to claim 18, wherein the inflating step is carried out with a balloon (18) whose diameter, when inflated, is equal to or greater than the diameter of the circumferential cuff (24) of the tracheal tube (20) when the circumferential cuff (24) is uninflated.

20. The method according to claim 16, wherein the method is carried out with a dilator tube (12) which carries the balloon catheter (16) and the tracheal tube (20) thereon, and wherein the inserting step comprises advancing the dilator tube (12), the balloon catheter (16) and the tracheal tube (20) together along the wire guide (54), without any longitudinal movement of the dilator tube (12), the balloon catheter (16) and the tracheal tube (20) relative to one another.

* * * * *